United States Patent [19]

Cianci

[11] Patent Number: 4,579,126

[45] Date of Patent: Apr. 1, 1986

[54] LIQUID DRAINAGE SYSTEM WITH EMPTYING SYSTEM

[75] Inventor: James P. Cianci, Cary, Ill.

[73] Assignee: The Kendall Company, Boston, Mass.

[21] Appl. No.: 696,367

[22] Filed: Jan. 30, 1985

Related U.S. Application Data

[63] Continuation of Ser. No. 471,968, Mar. 4, 1983, abandoned.

[51] Int. Cl.[4] ........................ A61B 5/00; B65D 33/00; B65D 81/00
[52] U.S. Cl. .................................. 128/767; 128/771; 604/323
[58] Field of Search ............... 128/760, 762, 766, 767, 128/771; 604/317–328; 73/219, 223, 215, 861

[56] References Cited

U.S. PATENT DOCUMENTS

| | | | |
|---|---|---|---|
| Re. 26,964 | 10/1970 | Coanda | 128/2 |
| 3,345,980 | 10/1967 | Coanda | 128/762 |
| 3,601,119 | 8/1971 | Engelsher | 604/323 |
| 3,961,529 | 6/1976 | Hanfl | 73/219 |
| 4,178,934 | 12/1979 | Forman | 128/295 |
| 4,265,243 | 5/1981 | Taylor | 128/767 |
| 4,305,290 | 12/1981 | Taylor | 128/762 |

FOREIGN PATENT DOCUMENTS 0008450  8/1979  European Pat. Off. ............ 604/318

Primary Examiner—J. L. Kruter
Attorney, Agent, or Firm—Powell L. Sprunger

[57] ABSTRACT

A liquid drainage system comprising, a urine meter comprising a first container having a compartment to receive the liquid, and a second container having a cavity alongside the first container, with the first container having an opening adjacent an upper portion of the first container communicating between the compartment and cavity to permit passage of liquid between the compartment and cavity. The system has a receptacle having a chamber supported below the urine meter, a first conduit communicating between the compartment and receptacle chamber, and a second conduit communicating between the cavity and the receptacle chamber. The system has a device for simultaneously opening and closing the first and second conduits to empty the contents of the compartment and cavity into the receptacle chamber.

6 Claims, 4 Drawing Figures

LIQUID DRAINAGE SYSTEM WITH EMPTYING SYSTEM

This is a continuation division of application Ser. No. 471,968, filed Mar. 4, 1983 now abandoned.

BACKGROUND OF THE INVENTION

The present invention relates to liquid drainage systems, and more particularly to urine drainage systems.

In the past, urine drainage systems have been known. Such systems may comprise a catheter which is passed through the urethra of a patient until a distal end of the catheter is located in the patient's bladder, a drainage tube connected to a proximal end of the catheter outside the patient's body, and a container having a compartment with a downstream end of the drainage tube communicating with the compartment. In use, urine drains through the catheter and drainage tube into the compartment.

In one form, the container may comprise a urine meter, and a receptacle may be supported below the container. During use of the system, it may be desirable to empty the container into the receptacle in a simple manner.

SUMMARY OF THE INVENTION

A principal feature of the present invention is the provision of an improved liquid drainage system of simplified construction.

The liquid drainage system of the present invention comprises, a urine meter comprising a first container having a compartment to receive the liquid, and a second container having a cavity alongside the first container, with the first container having opening means adjacent an upper portion of the first container communicating between the compartment and cavity to permit passage of liquid between the compartment and cavity. The system has a receptacle having a chamber supported below the urine meter, a first conduit communicating between the compartment and receptacle chamber, and a second conduit communicating between the cavity and receptacle chamber.

A feature of the present invention is the provision of means for simultaneously opening and closing the first and second conduits.

Another feature of the invention is that the opening and closing means permits emptying of the contents of the compartment and cavity into the receptacle chamber.

Still another feature of the invention is that the opening and closing means permits quick drainage of the first and second containers into the receptacle.

Another feature of the invention is that the opening and closing means is at a fixed position such that the first and second containers are emptied without affecting the calibrated volume of urine collected in the first and second containers.

Further features will become more fully apparent in the following description of the embodiments of this invention and from the appended claims.

DESCRIPTION OF THE PREFERRED EMBODIMENTS

Figure 1:
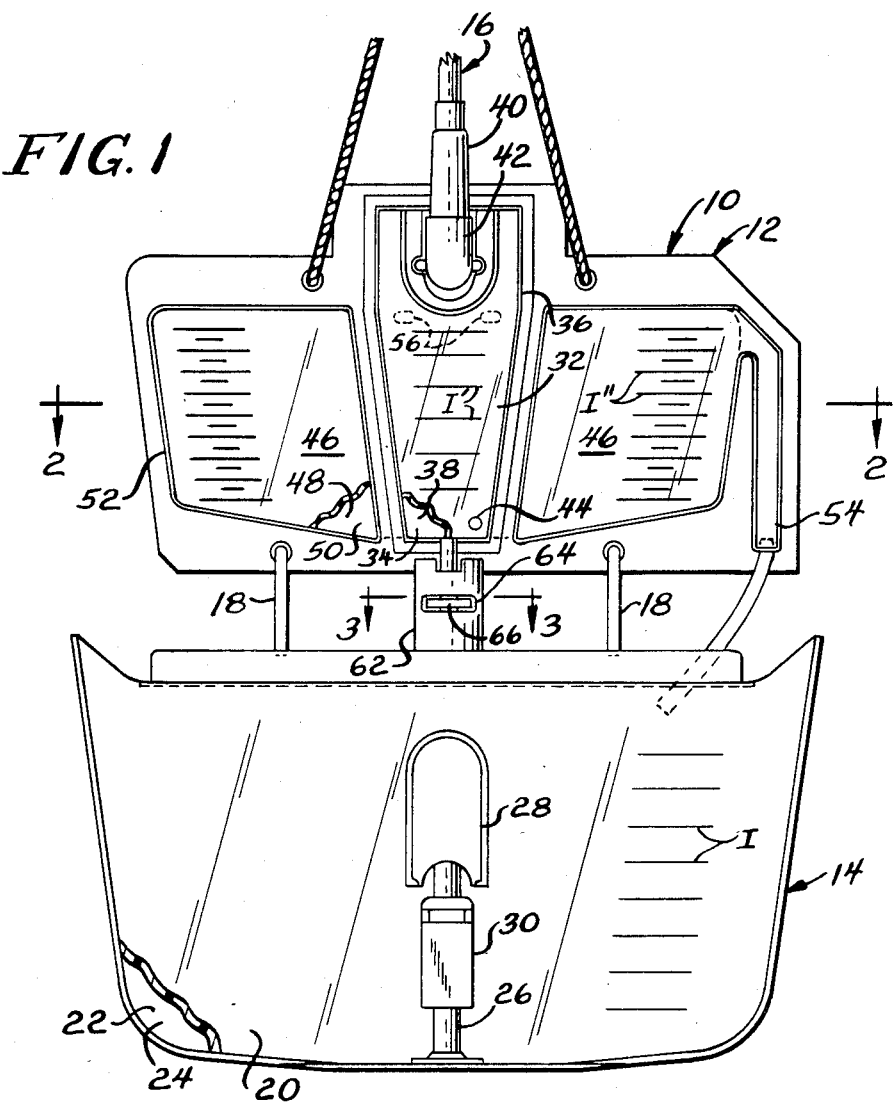
FIG. 1 is a fragmentary elevational view of a liquid drainage system of the present invention.

Referring now to FIG. 1, there is shown a liquid drainage system generally designated 10 having a urine meter 12, a receptacle 14, and a drainage tube 16. As shown, the receptacle 14 is supported below the urine meter 12 by a pair of ties 18 which extend from a lower portion of the urine meter 12 to an upper portion of the receptacle 14. The receptacle 14 has a transparent front wall 20 of flexible plastic material, and a back wall 22 of flexible plastic material, with the front and back walls 20 and 22 being joined at their periphery in order to define a chamber 24 between the front and back walls 20 and 22. The receptacle 14 may have a lower tubular section 26 communicating with a lower portion of the chamber 24, with the outer end of the tubular section 26 being received in a pocket 28 in a storage position of the tubular section 26. When it is desired to empty liquid from the chamber 24, the tubular section 26 is removed from the pocket 28 and a clamp 30 of known type is opened to permit passage of the liquid through the tubular section 26. When drainage of the chamber 24 has been completed, the clamp 30 is closed, and the outer end of the tubular section 26 is inserted into the pocket 28 in order to place the tubular section 26 in the storage position. As shown, the front wall 20 may have vertically spaced indicia I to determine the volume of urine in the chamber 24 through the transparent front wall 20.

Figure 2:
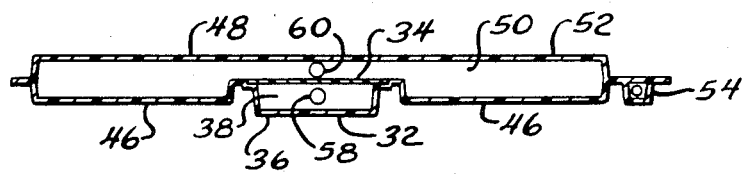
FIG. 2 is a sectional view taken substantially as indicated along the line 2—2 of FIG. 1.

With reference to FIGS. 1 and 2, the urine meter 12 comprises a rigid header for the receptacle 14. The urine meter 12 has a transparent rigid central front wall 32, and an intermediate rigid wall 34 which forms a first container 36 defining a compartment 38. The urine meter 32 has a connector 42 secured to an upper portion of the front wall 32, with a downstream end 40 of the drainage tube 16 being secured to the connector 42, such that the drainage tube 16 communicates with the compartment 38. The front wall 32 has an elastic plug 44 extending through a lower portion of the front wall 32, such that a needle on a syringe may be passed through the plug 44 in order to obtain a sample of the urine in the compartment 38.

The urine meter 12 has a transparent rigid front wall 46 on opposed sides of the first container 36, and a rigid back wall 48 secured to the front wall 46 around the periphery of the front and back walls 46 and 48, such that the front wall 46, back wall 48, and intermediate wall 34 form a second container 52 defining a cavity 50, with a major portion of the cavity 50 being located on opposed sides of the first container 36. As shown, the system 10 has a tubular section 54, with an upper portion of the tubular section 54 communicating with an upper portion of the cavity 50, and with a lower portion of the tubular section 54 communicating with an upper portion of the chamber 24, such that the tubular section 54 communicates between the cavity 50 and chamber 24. The intermediate wall 34 of the first container 36 has one or more openings 56 adjacent an upper portion of the first container 36 communicating between the compartment 38 and the cavity 50 in order to permit passage of liquid from the compartment 38 into the cavity 50. The front wall 32 of the first container 36 has indicia I' which indicates the volume of urine collected in the compartment 38 as viewed through the transparent front wall 32. Also, the front wall 46 of the second container 52 has indicia I" to indicate the volume of urine collected in the cavity 50 as viewed through the transparent front wall 46.

The system 10 has a first conduit 58 of elastic material, such as rubber, communicating between a lower portion of the compartment 38 and an upper portion of the receptacle chamber 24. The system 10 also has a second conduit 60 of elastic material, such as rubber, which is aligned in a side by side relationship with the first conduit 58, and communicating between a lower portion of the cavity 50 and an upper portion of the receptacle chamber 24. With reference to FIGS. 1-4, the system 10 has a cylindrical housing 62 of suitable rigid plastic material located intermediate the urine meter 12 and the receptacle 14, with the housing 62 surrounding the first and second conduits 58 and 60. As shown, the housing 62 has a slot 64 extending therethrough, and an elongated clamp member 66 of suitable rigid plastic material slidably received in the slot 64 of the housing 62. The clamp member 66 has an elongated opening 68 which receives the first and second conduits 58 and 60. The opening 68 has a first portion 70 adjacent one end of the clamp nember 66 having dimensions larger than the first and second conduits 58 and 60, and a second portion 72 adjacent the other end of the clamp member 66 having dimensions more narrow than the first and second conduits 58 and 60. With reference to FIG. 4, the clamp member 66 is movable between a first position with the first and second conduits 58 and 60 in register with the first opening portion 70, such that the first and second conduits 58 and 60 are simultaneously opened, and, with reference to FIG. 3, a second position with the first and second conduits 58 and 60 in register with the second opening portion 72 in order to simultaneously close the first and second conduits 58 and 60 which are pinched in the second opening portion 72.

Figure 3:
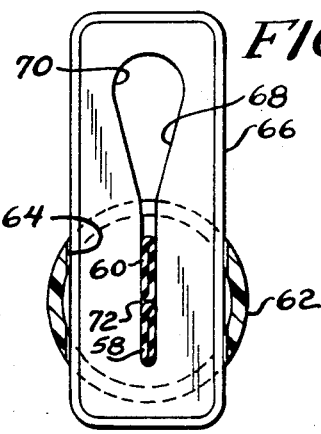
FIG. 3 is a sectional view taken substantially as indicated along the line 3—3 illustrating a clamp member in a closed position.
Figure 4:
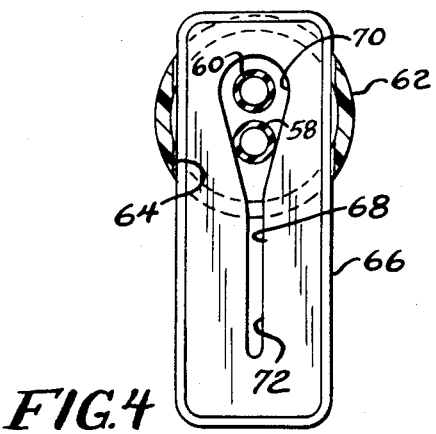
FIG. 4 is a sectional view illustrating the clamp member of FIG. 3 in an open position.

When it is desired to use the system 10, with reference to FIG. 3, the clamp member 66 is moved to the second position in order to simultaneously close the first and second conduits 58 and 60. A catheter (not shown) is passed through the urethra of a patient until a distal end of the catheter is located in the patient's bladder. A proximal end of the catheter located outside the patient's body is connected to an upstream end of the drainage tube 16, and urine drains through the catheter and drainage tube 16 into the compartment 38 of the first container 36 for collection therein. As urine collects in the compartment 38, the level of collected urine will eventually reach the openings 56, after which the urine will pass from the compartment 38 through the openings 56 into the cavity 50 of the second container 52 for collection therein. If a sufficient quantity of urine is collected in the cavity 50, the urine will eventually overflow through the tubular section 54 into the receptacle chamber 24 for collection in the receptacle 14. When it is desired to empty the contents of the compartment 38 and cavity 50 into the receptacle chamber 24, with reference to FIG. 4, the clamp member 66 is moved to the first position in order to simultaneously open the first and second conduits 58 and 60 and permit passage of collected urine from the compartment 38 and cavity 50 through the first and second conduits 58 and 60 into the receptacle chamber 24. After the emptying procedure of the compartment 38 and cavity 50 has been completed, with reference to FIG. 3, the clamp member 66 is again moved to the second position in order to close the conduits 58 and 60 and start collection of urine in the compartment 38 and the cavity 50 anew.

Thus, in accordance with the present invention, a liquid drainage system 10 is disclosed in which the collected contents of a compartment 38 and cavity 50 of a urine meter 12 may be simultaneously emptied in a simplified manner through first and second conduits 58 and 60 into a receptacle chamber 24. In accordance with the present invention, the housing 62 maintains the clamp member 66 at a fixed vertical position, in order to prevent modification of the calibrated volume of urine in the compartment 38 and cavity 50.

The foregoing detailed description is given for clearness of understanding only, and no unnecessary limitations should be understood therefrom, as modifications will be obvious to those skilled in the art.

I claim:

1. A drainage system for urine, comprising:
   a urine meter comprising a first container with two opposed sides having a compartment to receive the urine, a second container having a cavity on said opposed sides of the first container, said first container having opening means adjacent an upper portion of the first container fluidly communicating between the compartment and cavity to permit passage of urine between the compartment and cavity, and an overflow tubular section fluidly communicating with an upper portion of the cavity;
   an independent receptacle having a receiving chamber with an upper portion supported below the urine meter, with said tubular section fluidly communicating with the chamber; and the compartment having a first conduit which directly fluidy communicates between a lower portion of the compartment and said upper portion of the receptacle chamber and a second conduit which fluidly communicates directly between a lower portion of the cavity and said upper portion of said receptacle chamber;
   valve means for on said first and second conduits, simultaneously directly emptying the compartment and cavity from a lower part of the compartment and cavity separately from the tubular section into said receptacle chamber.

2. The system as in claim 1 wherein said first and second conduits are substantially parallel to each other.

3. The system of claim 2 wherein said first and second containers are rigid.

4. The system of claim 2 wherein said first and second conduits are elastic and aligned in a side by side relationship, and in which said opening and closing means which forms a valve means which comprises a housing intermediate the urine meter and receptacle and surrounding the first and second conduits, with said housing having a slot, and a clamp member slidably received in said slot, said clamp member having an opening to receive the first and second conduits, said opening having a first portion being sufficiently large to permit opening of the first and second conduits, and a second portion being sufficiently narrow to close the first and second conduits, said clamp member being movable between a first position with the first opening portion registered with the first and second conduits to open the first and second conduits, and a second position with the second opening portion registered with the first and second conduits to close the first and second conduits.

5. The system of claim 4 wherein the first opening portion is located adjacent one end of the clamp member, and in which the second opening portion is located adjacent the other end of the clamp member.

6. The system of claim 2 wherein the opening and closing means is at a fixed position relative the compartment and cavity.

* * * * *

UNITED STATES PATENT AND TRADEMARK OFFICE
CERTIFICATE OF CORRECTION

PATENT NO. : 4,579,126
DATED : April 1, 1986
INVENTOR(S) : James P. Cianci

It is certified that error appears in the above-identified patent and that said Letters Patent are hereby corrected as shown below:

Column 1, line 5, delete "division".

Column 1, line 57, "volune" should be -- volume -- .

Column 4, line 37, "fluidy" should be -- fluidly -- .

Column 4, lines 44-45, delete "valve means for on said first and second conduits, simultaneously directly" and insert therefor -- valve means on said first and second conduits for simultaneously selectively directly -- .

Signed and Sealed this

Twenty-second Day of July 1986

[SEAL]

Attest:

DONALD J. QUIGG

Attesting Officer　　Commissioner of Patents and Trademarks